United States Patent [19]
Winter

[11] 3,942,194
[45] Mar. 9, 1976

[54] PROSTHETIC DEVICE FOR HANDICAPPED PERSONS

[76] Inventor: Sybil Betty Anna Winter, 10124 W. Capitol Drive, Milwaukee, Wis. 53222

[22] Filed: Aug. 30, 1974

[21] Appl. No.: 501,950

[52] U.S. Cl. .............................. 3/1; 3/12.8; 401/8
[51] Int. Cl.² ........................ A61F 1/00; A61F 1/06
[58] Field of Search .............. 3/12, 12.8, 1; 401/6, 8

[56] References Cited
UNITED STATES PATENTS
2,889,160   6/1959   Nelson .............................. 3/12.8 X

*Primary Examiner*—Ronald L. Frinks
*Attorney, Agent, or Firm*—Wheeler, Morsell, House & Fuller

[57] ABSTRACT

Two stiff discs are rotatably attached together in face-to-face contact, one of the discs having a ring of openings therein, and the other disc having a nipple positioned to engage and latch in the openings. An implement holder is attached to one of the discs and a strap is attached to the other disc for strapping the two discs and implement holder to a person's hand. By rotating the disc carrying the implement holder with respect to the other disc, and clamping it in the desired position, the implement holder can be oriented in the proper rotary position for use of a predetermined implement by the person. The implement can be a knife, fork, comb, tooth brush, or any other suitable implement. The discs can be strapped to the palm of the person's hand, to the back of the hand, or to the wrist.

7 Claims, 5 Drawing Figures

U.S. Patent  March 9, 1976  3,942,194
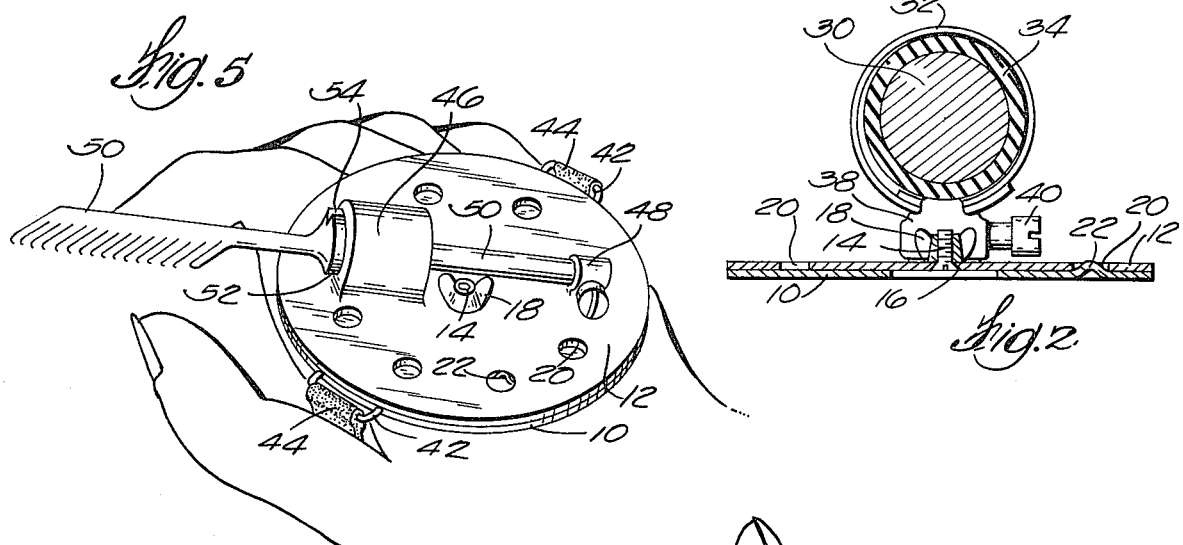
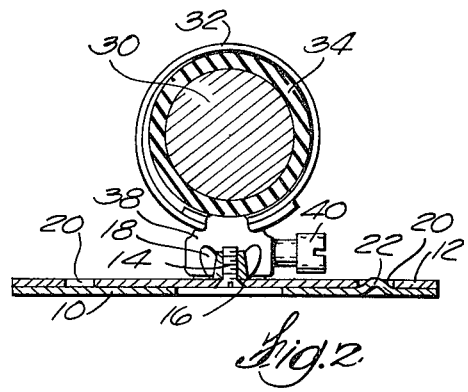
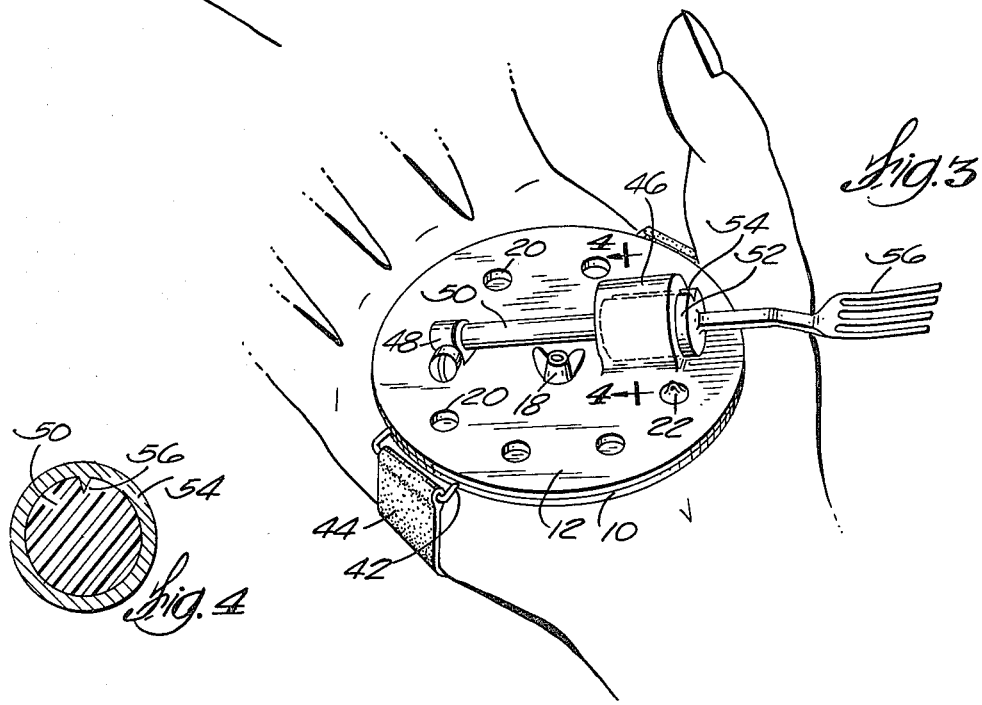
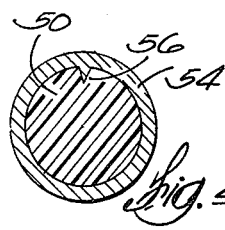
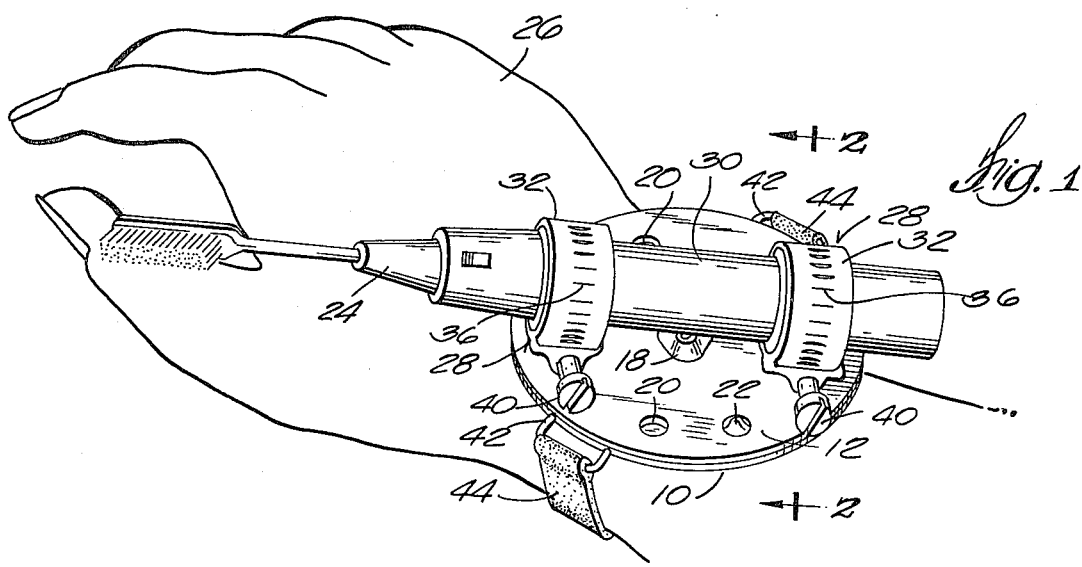

PROSTHETIC DEVICE FOR HANDICAPPED PERSONS

BACKGROUND OF THE INVENTION

This invention relates to prosthetic devices for persons whose fingers are wholly or partially paralyzed but who are able to move their arms. In the past, prosthetic devices have been made for such persons to enable them to hold and to use common implements such as combs, forks, and the like. One such prosthetic device is disclosed in U.S. Pat. No. 2,889,160 to Nelson. Other prosthetic devices for persons with missing hands or fingers are disclosed in the following U.S. Pat. Nos.

| | |
|---|---|
| Darrance | 953,821 |
| Lux | 2,561,523 |
| Ameline | 2,666,928 |
| Saverino | 3,434,163 |
| Perex | 3,490,078 |

This invention is directed to better prosthetic devices and has as its principal object to provide a prosthetic device which is simpler, less expensive, and more effective than those heretofore known. Other objects and advantages of the invention will become apparent to those skilled in the art from the description herein.

SUMMARY OF THE INVENTION

This invention includes an implement holder for holding a knife, fork, spoon, comb, tooth brush, dental floss holder or any other hand implement. The implement holder is attached to a stiff disc which is rotatably attached to another stiff disc in face-to-face contact therewith. A strap is attached to one of the discs for strapping the two discs and implement holder to a person's hand or wrist. Means is provided for latching the two discs to each other in any one of a predetermined plurality of rotary positions whereby the implement holder can be oriented in the proper rotary position for use of a predetermined implement by the person wearing the device.

DESCRIPTION OF THE DRAWINGS

FIG. 1 is a perspective view of one illustrative embodiment of the invention strapped to a person's wrist with an electric tooth brush in the implement holder thereof.

FIG. 2 is a cross-sectional view taken on the line 2—2 of FIG. 1.

FIG. 3 is a perspective view of a second embodiment of the invention strapped to the palm of a person's hand with a fork in the implement holder thereof.

FIG. 4 is a cross-sectional view taken on the line 4—4 of FIG. 3.

FIG. 5 is a perspective view of the embodiment of FIG. 3 strapped to the back of a person's hand with a comb in the implement holder thereof.

DESCRIPTION OF THE PREFERRED EMBODIMENTS

Although the disclosure hereof is detailed and exact to enable those skilled in the art to practice the invention, the physical embodiments herein disclosed merely exemplify the invention which may be embodied in other specific structure. While the best known embodiment has been described, the details may be changed without departing from the invention, which is defined by the claims.

Referring to FIGS. 1 and 2, one embodiment of the invention includes two stiff metal discs 10 and 12 which are rotatably mounted in face-to-face relationship with each other by means of a threaded stud 14 (FIG. 2) which is welded to the center of lower disc 10 and extends through a central hole 16 in upper disc 12. A wing nut 18 is engaged on the exposed end of stud 14 and can be tightened to clamp discs 10 and 12 together as tightly as needed with no tools and limited dexterity. A ring of holes 20 is formed in upper disc 12 and a nipple 22 is formed in lower disc 10 and is positioned to engage the holes 20 in disc 12. Holes 20, nipple 22, stud 14, hole 16 and wing nut 18 taken together form means for latching discs 10 and 12 together in any one of a predetermined plurality of rotary positions for the purpose of adjusting the orientation of an implement such as electric tooth brush 24 with respect to the person's hand 26 upon which the device of this invention is strapped, the resilience of the discs securing them while permitting turning to a new position.

An implement holder including two circular screw-adjustable clamps 28 is used to attach the barrel 30 of tooth brush 24 to upper disc 12. Each of the clamps 28 include a strap 32 adjustable in diameter and disposed around an annular resilient ring 34 which is dimensioned to slideably receive the barrel 30 of tooth brush 24. A second set of clamps 28 may be provided at right angles to the first set with different diameters to receive tools not within the adjustment range of the set illustrated or to receive specially adapted tool shafts as disclosed below. Each of the straps 32 have openings 36 formed therein for engaging a conventional screw or worm (not visible-such as is found in hose clamps) contained in housing 38 (FIG. 2) and rotated by screw head 40 to tighten or loosen straps 32. Clamps are well known prior art mechanisms which are available in various sizes. Smaller size clamps 28 can be employed to hold the handle of a standard manually operated tooth brush if desired. Clamps 28 are desirably welded to upper disc 12.

A pair of loops 42 (FIG. 1) are provided on opposite sides of lower disc 10 and a strap 44 including a standard buckle (not visible) is attached to loops 42 for strapping the device to a person's hand or wrist. FIG. 1 shows the device strapped to a person's wrist while FIGS. 3 and 5 shows another embodiment strapped to the palm and back of a person's hand, respectively. Any of these three positions can be used depending on the nature of the handicap and on the implement employed.

To use the device, the clamps 28 are first oriented in the proper angular orientation to direct tooth brush 24 in the right direction for easy and effective brushing of the teeth. This is done by rotating disc 12 to the proper rotary position with respect to loops 42, and then adjusting wing nut 18 (if required) after nipple 22 engages the desired opening 20. The barrel 30 of tooth brush 24 is then slid into resilient rings 34. If necessary, screws 40 are turned until clamps 28 are tight enough to frictionally hold tooth brush 24 in position during use. The device is then strapped to the handicapped person's hand or wrist and toothpaste is applied to toothbrush 24 in preparation for brushing the teeth. One important feature of this invention is that it permits the handicapped person to brush in hard to reach locations and thereby to preserve the health of the oral tissues and teeth.

FIGS. 3–5 show a modification of the above described embodiment in which the implement holder includes a hollow cylinder 46 and a small circular screw-adjustable clamp 48 which are attached to disc 12 in spaced apart locations and are oriented to receive a special implement mounted on a cylindrical shaft 50 and an enlarged, grooved cylindrical hub 52. The groove 54 of hub 52 is dimensioned to engage a rib 56 (FIG. 4) in the interior of hollow cylinder 46 which prevents the implement shaft 50 from rotating. The implement supported by shaft 50 and hub 52 can be a fork 56 (FIG. 3), a comb 50 (FIG. 5), or any other hand implement such as a knife, spoon, tooth brush, dental floss holder, cosmetic applicator, or the like, all of which are mounted on a shaft 50 and hub 52 so that they will fit in the above described implement holder. With such implements, the handicapped person will be able to perform numerous manual operations that would otherwise have to be performed by someone else.

The discs 10 and 12 are here described as metal, as are clamps 28 and 48, but it will be apparent that other materials can be used. The latching device can likewise be varied although that shown is particularly well suited to the invention. The attached claims define the scope of the invention.

I claim:

1. A prosthetic device comprising a first stiff disc, a second stiff disc rotatably attached in face-to-face contact with said first disc, an implement holder attached to said second disc and rotatable therewith, a strap attached to said first disc for strapping the two discs and implement holder to a person's hand, means for latching said discs together in any one of a predetermined plurality of rotary positions whereby said implement holder can be oriented in the proper rotary position for use of a predetermined implement by said person, said implement holder comprising at least a pair of circular clamps attached to said second disc.

2. A prosthetic device as defined in claim 1 wherein said circular clamps are of adjustable circumference and lined with resilient material for frictional retention of tool shafts.

3. A prosthetic device as defined in claim 1 and further comprising an annular resilient ring contained within each said circular clamp.

4. A prosthetic device comprising a first stiff disc, a second stiff disc rotatably attached in face-to-face contact with said first disc, an implement holder attached to said second disc and rotatable therewith, a strap attached to said first disc for strapping the two discs and implement holder to a person's hand, and means for latching said discs together in any one of a predetermined plurality of rotary positions whereby said implement holder can be oriented in the proper rotary position for use of a predetermined implement by said person, said implement holder comprising a hollow cylinder and a circular clamp attached to said second disc, and further comprising an implement having a hub at one end which is fitted in a single orientation within said hollow cylinder.

5. A prosthetic device as defined in claim 4 wherein said hollow cylinder contains a rib extending longitudinally in the interior thereof and wherein said hub is slotted to engage said rib and thereby prevent rotation of the corresponding implement.

6. A prosthetic device comprising a first stiff disc, a second stiff disc rotatably attached in face-to-face contact with said first disc, an implement holder attached to said second disc and rotatable therewith, a strap attached to said first disc for strapping the two discs and implement holder to a person's hand, means for latching said discs together in any one of a predetermined plurality of rotary positions whereby said implement holder can be oriented in the proper rotary position for use of a predetermined implement by said person, said latching means including a ring of openings in one of said discs and a nipple in the other disc, said nipple being positioned to engage said openings, and means for clamping said discs together.

7. A prosthetic device as defined in claim 6 wherein said discs are rotatably attached together by a threaded stud attached to the center of one disc and projecting outwardly therefrom and a central opening in the other disc for receiving said threaded stud, said discs being joined together in face-to-face contact with said stud extending through said central opening, and wherein said means for clamping said discs together comprises a wing nut engageable with said threaded stud.

* * * * *